United States Patent [19]

Hamada et al.

[11] Patent Number: 5,113,002

[45] Date of Patent: May 12, 1992

[54] POLYSILANE COPOLYMERS AND METHOD FOR PREPARING SAME

[75] Inventors: Yoshitaka Hamada, Annaka, Japan; Robert West, Madison, Wis.

[73] Assignee: Shin-Etsu Chemical Co., Ltd., Tokyo, Japan

[21] Appl. No.: 629,630

[22] Filed: Dec. 18, 1990

[51] Int. Cl.$^5$ .................................................. C07F 7/08
[52] U.S. Cl. ..................................................... 556/431
[58] Field of Search ........................................ 556/431

[56]  References Cited

U.S. PATENT DOCUMENTS

| | | | |
|---|---|---|---|
| 2,551,924 | 5/1951 | Boldebrick | 556/431 |
| 4,395,562 | 7/1983 | Yobji et al. | 556/431 |

FOREIGN PATENT DOCUMENTS

| | | | |
|---|---|---|---|
| 0105429 | 9/1978 | Japan | 556/431 |
| 0122387 | 9/1981 | Japan | 556/431 |
| 0122388 | 9/1981 | Japan | 556/431 |

Primary Examiner—Paul F. Shaver
Attorney, Agent, or Firm—Birch, Stewart, Kolasch & Birch

[57]  ABSTRACT

A polysilane copolymer of the general formula:

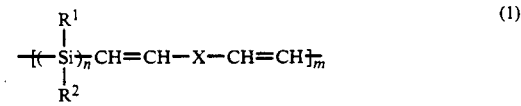

(1)

wherein $R^1$ and $R^2$ each are an alkyl group having 1 to 6 carbon atoms or an aryl group having 6 to 12 carbon atoms, X is an alkylene group having 1 to 6 carbon atoms, an arylene group having 6 to 12 carbon atoms or a silanylene group having 1 to 6 silicon atoms, n is an integer of at least 1, and m is an integer of at least 1. The copolymer is synthesized by the hydrosilylation polymerization of a dihydrosilane compound H—(SiR$^1$R$^2$)$_n$—H with a diacetylenyl compound HC≡C—X—C≡CH.

6 Claims, No Drawings

POLYSILANE COPOLYMERS AND METHOD FOR PREPARING SAME

This invention relates to novel polysilane copolymers and a method for preparing the same.

BACKGROUND OF THE INVENTION

Polysilane is one of the "hot" materials in current research and development because of its peculiar structure and interesting physical and chemical properties. One problem in developing this material is preparation method. The common method which utilizes Wults coupling reaction by alkali metal requires a reaction temperature as high as about 110° C. and very drastic reaction conditions. This synthetic problem limits the substituents on polysilane polymers. The other known preparation methods are not very effective to synthesize polysilane polymers having a high molecular weight.

As for the preparation of polysilane copolymers, in turn, copolymers of polysilane with polythiophene and polyphenylene were reported although copolymers having a high molecular weight were not available. Most methods for the preparation of copolymers of polysilane with ethylene, acetylene, and phenylene utilize either Wults coupling reaction or lithium acetylide and thus require drastic reaction conditions. It is known in the art to prepare high polymers through ring-opening reaction under mild conditions, for example, using benzosilacyclobutene as proposed by Shiina et. al. and using tetrasilacycloocta-1,5-diine as proposed by West et. al. These methods are able to introduce only disilanyl unit in the polymers. It is thus desired to introduce a longer polysilane chain for obtaining copolymers possessing more the character of polysilane.

SUMMARY OF THE INVENTION

An object of the present invention is to provide a new and improved polysilane copolymer having two vinyl groups to which various function groups can be added or introduced. Another object of the present invention is to provide a method for preparing such a novel polysilane copolymer by hydrosilylation polymerization.

According to one aspect of the present invention, there is provided a polysilane copolymer of the general formula:

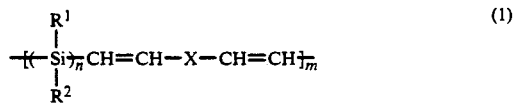

wherein
R$^1$ and R$^2$ independently represent an alkyl group having 1 to 6 carbon atoms or an aryl group having 6 to 12 carbon atoms,
X represents an alkylene group having 1 to 6 carbon atoms, an arylene group having 6 to 12 carbon atoms or a silanylene group having 1 to 6 silicon atoms,
letter n is an integer of at least 1, and
m is an integer of at least 1.

According to another aspect of the present invention, there is provided a method for preparing a polysilane copolymer of formula (1) comprising the step of reacting a silane compound of the general formula:

with a diacetylenyl compound of the general formula:

$$HC \equiv C-X-C \equiv CH \quad (3)$$

wherein R$^1$, R$^2$, X and n are as defined above.

The method for preparing polysilane copolymers in accordance with the present invention uses both-end hydrogen functional polysilane oligomers or $\alpha,\omega$-dihydrooligosilanes for hydrosilylation polymerization with $\alpha,\omega$-diacetylenyl compounds, ensuring that polysilane oligomers of any chain length are useful as long as they have hydrogen replaced at either end. There can be synthesized polysilane copolymers effectively exhibiting the character of polysilane if longer polysilane chains are used. The longer the polysilane chain, the better the character of polysilane appears. In this respect, polysilane copolymers having pentasilane or hexasilane unit are quite advantageous. In addition, the method of the invention can synthesize of polysilane copolymers through hydrosilylation reaction which requires relatively mild conditions, allowing for development of the character of polysilane and easy introduction of functional groups which are otherwise difficult to introduce.

The novel polysilane copolymers of the invention have two vinyl groups to which various functional groups can be added. The polysilane copolymers may find application as electronic materials, photoconductive materials, nonlinear optical materials, and oxygen enriching membranes.

DETAILED DESCRIPTION OF THE INVENTION

The novel polysilane copolymers according to the present invention are of the general formula:

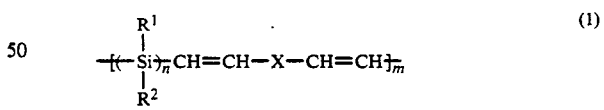

In formula (1), R$^1$ and R$^2$, which may be identical or different, independently represent an alkyl group having 1 to 6 carbon atoms such as methyl, ethyl, propyl, butyl, pentyl and hexyl groups, or an aryl group having 6 to 12 carbon atoms such as a phenyl group. Letter n is an integer of at least 1, preferably 2 to 6, more preferably 5 to 6.

X represents an alkylene group having 1 to 6 carbon atoms such as methylene, ethylene, propylene, butylene, pentylene and hexylene groups, an arylene group having 6 to 12 carbon atoms such as phenylene and dimethylphenylene groups, or a silanylene group having 1 to 6 silicon atoms, preferably 2 to 6 silicon atoms, represented by the formula:

$$\left(\begin{array}{c} R^1 \\ | \\ Si \\ | \\ R^2 \end{array}\right)_l$$

wherein $R^1$ and $R^2$ are as defined above and letter l is an integer of 1 to 6, preferably 2 to 6.

Letter m is an integer of at least 1, preferably at least 100. In general, larger values of m are preferred.

The polysilane copolymers of formula (1) can be synthesized by reacting a silane compound of the general formula:

$$H\left(\begin{array}{c} R^1 \\ | \\ Si \\ | \\ R^2 \end{array}\right)_n H \quad (2)$$

with a diacetylenyl compound of the general formula:

$$HC\equiv C-X-C\equiv CH \quad (3).$$

In formulae (2) and (3), $R^1$, $R^2$, X and n are as defined above.

The reaction or hydrosilylation polymerization can proceed without solvent although it is recommended to use an aprotic solvent such as tetrahydrofuran (THF), hexane, benzene, toluene, and xylene in order to obtain a polysilane copolymer having a higher molecular weight. The molar ratio of the silane compound of formula (2) to the diacetylenyl compound of formula (3) may range from 0.9:1.1 to 1.1:0.9, but is most often 1:1 for obtaining high molecular weight copolymers.

A catalyst is preferably used. Any known hydrosilylation catalysts including platinum or platinum compounds such as chloroplatinic acid can be used in a catalytic amount for hydrosilylation, preferably in an amount of about 0.05 to about 1% by weight of the reaction mixture.

The reaction temperature is generally in the range of $-80°$ C. to $130°$ C., preferably $10°$ to $110°$ C., most often from room temperature to the solvent reflux temperature. Reaction may be continued until Si—H and acetylenic protons are consumed and a corresponding amount of vinyl protons appear. The reaction time is usually about 10 minutes to about 10 hours.

EXAMPLE

Examples of the present invention are given below by way of illustration and not by way of limitation.

EXAMPLE 1

Reaction was carried out by dissolving 700 mg (2 mmol) of 1,6-dihydrododecamethylhexasilane and 308 mg (2 mmol) of 2,5-dimethyl-1,4-diethynylbenzene in 10 ml of tetrahydrofuran (THF), and adding 0.04 mg of chloroplatinic acid in THF thereto. Exothermic reaction immediately proceeded under THF reflux while the reaction mixture turned brown. After 3 hours of reaction, the reaction mixture was cooled down and the solvent distilled off. The residue or polymer was analyzed to have a molecular weight of about 65,000 by gas permeation chromatography (GPC) using polystyrene standard. Proton NMR showed the disappearance of Si—H and HC≡C signals and the formation of broad HC=C. The resulting polymer was thus identified to have the following structural formula:

$$\left(\begin{array}{c} CH_3 \\ | \\ Si \\ | \\ CH_3 \end{array}\right)_6 CH=CH-\underset{CH_3}{\overset{H_3C}{\bigcirc}}-CH=CH\Big)_m$$

wherein m is a number providing a molecular weight of about 65,000.

EXAMPLE 2

Reaction was carried out by dissolving 368 mg (2 mmol) of diphenylsilane and 252 mg (2 mmol) of 1,4-diethylnylbenzene in 10 ml of toluene, and adding 0.04 mg of chloroplatinic acid in isopropyl alcohol thereto. Exothermic reaction immediately proceeded under toluene reflux while the reaction mixture turned brown. After overnight reflux, the reaction mixture was cooled down and the solvent distilled off. The residue or polymer was analyzed to have a molecular weight of about 25,000 by GPC. The resulting polymer was identified to have the following structural formula:

$$\left(\begin{array}{c} C_6H_5 \\ | \\ Si-CH=CH-\bigcirc-CH=CH \\ | \\ C_6H_5 \end{array}\right)_m$$

wherein m is a number providing a molecular weight of about 25,000.

EXAMPLE 3

The procedure of Example 2 was repeated except that 484 mg (2 mmol) of 1,2-diphenyl-1,2-dimethylsilane and 580 mg (2 mmol) of 1,2-diethynyl-1,2-diphenyl-1,2-dimethyldisilane were used. There was obtained a polymer of the following structural formula having a molecular weight of about 1,200:

$$\left(\begin{array}{c} CH_3 \\ | \\ Si \\ | \\ C_6H_5 \end{array}\right)_2 CH=CH\left(\begin{array}{c} CH_3 \\ | \\ Si \\ | \\ C_6H_5 \end{array}\right)_2 CH=CH\Big)_m$$

wherein m is a number providing a molecular weight of about 1,200.

EXAMPLE 4

The procedure of Example 1 was repeated except that 1,5-dihydrodecapropylpentasilane and 2,5-dimethyl-1,4-diethynylbenzene were used. There was obtained a polymer of the following structural formula having a molecular weight of about 1,200:

$$\left(\begin{array}{c} C_3H_7 \\ | \\ Si \\ | \\ C_3H_7 \end{array}\right)_5 CH=CH-\underset{CH_3}{\overset{H_3C}{\bigcirc}}-CH=CH\Big)_m$$

EXAMPLE 5

The procedure of Example 1 was repeated except that 1,5-dihydrodecapropylpentasilane and 1,4-diethynylbenzene were used. There was obtained a polymer of the following structural formula having a molecular weight of about 2,500:

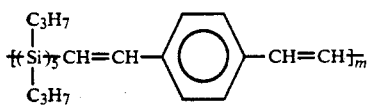

wherein m is a number providing a molecular weight of about 2,500.

For all the polymers of Examples 2 to 5, $^1$H NMR showed the consumption of Si-H and acetylenic protons and the appearance of vinyl protons.

EXAMPLE 6

The procedure of Example 1 was repeated except that 1,6-dihydrododecamethylhexasilane and 1,4-diethynylbenzene were used and the reaction temperature was room temperature. Exothermic reaction ceased in about 10 minutes, indicating substantial completion of polymerization. Removal of the solvent by distillation left a polymer which was insoluble in organic solvents.

Although some preferred embodiments have been described, many modifications and variations may be made thereto in the light of the above teachings. It is therefore to be understood that within the scope of the appended claims, the invention may be practiced otherwise than as specifically described.

We claim:

1. A polysilane copolymer of the general formula:

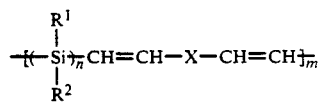

wherein
R$^1$ and R$^2$ independently represent an alkyl group having 1 to 6 carbon atoms or an aryl group having 6 to 12 carbon atoms,
X represents an alkylene group having 1 to 6 carbon atoms, an arylene group having 6 to 12 carbon atoms or a silanylene group having 1 to 6 silicon atoms,
letter n is an integer of at least 1, and
m is an integer of at least 1.

2. A method for preparing a polysilane copolymer of the general formula:

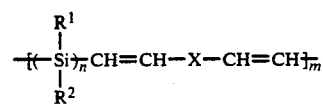

wherein R$^1$ and R$^2$ independently represent an alkyl group having 1 to 6 carbon atoms or an aryl group having 6 to 12 carbon atoms, X represents an alkylene group having 1 to 6 carbon atoms, an arylene group having 6 to 12 carbon atoms or a silanylene group having 1 to 6 silicon atoms, letter n is an integer of at least 1, and m is an integer of at least 1, said method comprising the step of:

reacting a silane compound of the general formula:

wherein R$^1$, R$^2$ and n are as defined above, with a diacetylenyl compound of the general formula:

wherein X is as defined above.

3. The polysilane copolymer according to claim 1, wherein X represents a phenylene group.

4. The polysilane copolymer according to claim 1, wherein said copolymer is selected from the group consisting of

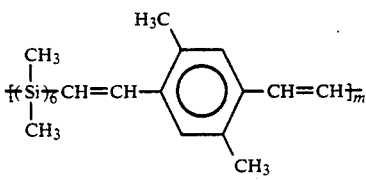

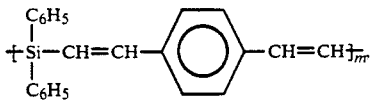

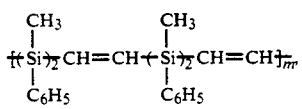

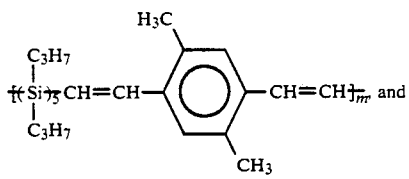

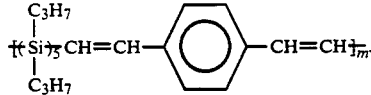

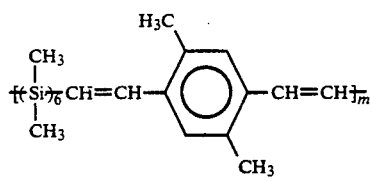

5. The method according to claim 2, wherein X represents a phenylene group.

6. The method according to claim 2, wherein the ratio of silane compound of formula (2) to diacetylenyl compound of formula (3) is from 0.9:1.1 to 1.1:0.9.

* * * * *